United States Patent [19]
Thomann et al.

[11] Patent Number: 5,428,291
[45] Date of Patent: Jun. 27, 1995

[54] DETERMINATION OF FLUID TRANSPORT PROPERTIES IN POROUS MEDIA BY NUCLEAR MAGNETIC RESONANCE MEASUREMENTS OF FLUID FLOW

[75] Inventors: Hans Thomann, Bedminster, N.J.; Michael Jerosch-Herold, Minneapolis, Minn.

[73] Assignee: Exxon Research and Engineering Company, Florham Park, N.J.

[21] Appl. No.: 86,392

[22] Filed: Jul. 1, 1993

[51] Int. Cl.⁶ .................................... G01R 33/20
[52] U.S. Cl. .................................... 324/303; 324/306
[58] Field of Search .............. 324/300, 303, 306, 307, 324/309; 128/653.2, 653.3

[56] References Cited

U.S. PATENT DOCUMENTS

| | | | |
|---|---|---|---|
| 4,728,892 | 3/1988 | Vinegar et al. | 324/303 |
| 4,752,734 | 6/1988 | Wedeen | 324/306 |
| 5,278,501 | 1/1994 | Guilfoyle | 324/306 |
| 5,289,124 | 2/1994 | Jerosch Herold et al. | 324/303 |

Primary Examiner—Sandra L. O'Shea
Assistant Examiner—Raymond Y. Mah
Attorney, Agent, or Firm—Ronald D. Hantman

[57] ABSTRACT

The present invention is a method to determine fluid transport properties of porous media by nuclear magnetic resonance measurements of fluid flow. The NMR signal is encoded by the fluid flow velocity from which the velocity spectrum and the fluid flow properties are obtained.

11 Claims, 7 Drawing Sheets

SINTERED GLASS BEADS
125 < r < 212 μm

DETERMINATION OF FLUID TRANSPORT PROPERTIES IN POROUS MEDIA BY NUCLEAR MAGNETIC RESONANCE MEASUREMENTS OF FLUID FLOW

BACKGROUND OF THE INVENTION

The present invention relates to methods for determining fluid flow properties of porous media by using nuclear magnetic resonance (NMR) in combination with magnetic field gradients to encode fluid molecule displacements. Examples of fluid flow properties include but are not limited to the measurement of the effective porosity, pore connectivity, distribution of flow velocities, and tortuosity of porous media such as naturally occuring rocks. In particular the present invention relates to measuring the fluid flow transport properties by nuclear magnetic resonance (NMR) using magnetic field gradients to encode the distribution of fluid flow velocities and to encode the spatial distribution of fluid flow in a porous material while a steady fluid pressure gradient is applied.

Nuclear magnetic resonance has been used for some time to study fluid flow [A. Caprihan and E. Fukushima, *Physics Reports*, 198, 195 (1990)]. In general fluid flow can be quantified with NMR by using switched magnetic field gradients. With the application of a magnetic field gradient the precession frequency of a magnetic moment (in this case the nuclear magnetic moment) is a function of position coordinate z in the direction of the applied field gradient:

$$\omega = \gamma(H_o + \vec{G} \cdot \vec{r}) \quad (1)$$

There exist several different classes of NMR experiments which quantitate flow: time-of-flight methods and phase encoding methods. For the heterogeneous media the phase encoding method is preferable, although the present invention does in principle work with both techniques. In the time of flight method spins in a slice of thickness and orientation determined by the applied gradient are prepared in a well defined state using rf pulses. After letting a time $\Delta$ elapse the distribution of transverse magnetization is imaged and from the observed displacements and time $\Delta$ one can calculate a velocity distribution spectrum. Time-of-flight techniques for measuring fluid flow are well established in medical application of magnetic resonance imaging (MRI) for MRI angiography.

In a phase encoding experiment the position of each fluid spin is tagged with a gradient pulse of duration $\delta$. After letting a time $\Delta$ elapse a gradient pulse of opposite polarity is applied. For stationary spins the phase acquired during the first gradient pulse is reversed by the second pulse which should be matched in duration and amplitude. For moving spins the phase reversal is incomplete depending on the displacement distance between the two gradient pulses. By repeating the experiment and systematically incrementing the amplitude of the matched gradient pulses one obtains a 2-d array of NMR signals as in an NMR imaging experiment. A Fourier transform of the data set of signals acquired with evenly incremented motion encoding gradient pulses will provide a spectrum of the distribution of fluid molecule displacements. There are numerous implementations of this measurement method. For porous media with low fluid flow permeability the stimulated echo sequence is most convenient for encoding slow flow as the duration $\Delta$ between gradient pulses is limited by the longitudinal relaxation time $T_1$, which is generally longer than the transverse relaxation time $T_2$. Furthermore this NMR pulse sequence is more suitable to the application of techniques for cancelation of constant magnetic background gradients, characteristic of heterogeneous systems such as porous media when they are placed in a magnetic field.

The present invention provides a method for obtaining at least one fluid transport properties of a porous material under steady flow conditions and encoding the fluid motion from the nuclear magnetic resonance (NMR) signal of the fluid molecules.

In one embodiment of the present invention, a flow velocity distribution spectrum is obtained, which shows the fraction of spins moving at a certain velocity through the pore space. From this the ratio of moving spins to stationary spins can be calculated and this ratio provides a measure of the effective porosity. The total porosity of a porous material is defined as the volume ratio of void space and grain space. For flow through porous media the pore space connectivity determines what fraction of fluid filling the pore space is movable. Fluid in isolated and dead ended pores does not move when an external pressure gradient is applied. Total porosity encompasses both the contribution from interconnected and isolated pores. Effective porosity measures the volume fraction of the interconnected part of pore space from which fluids can be recovered by application of pressure gradients. This parameter is of importance in oil reservoir modeling and the methods used to date for determination of the effective porosity involved time-consuming nuclear tracer techniques.

SUMMARY OF THE INVENTION

The present invention is a method for obtaining at least one fluid transport property of a porous material under steady flow conditions. The method includes the steps of saturating the porous material with a fluid and imposing a pressure gradient such that fluid flows through the porous medium. Radio frequency pulses are then applied leading to a coherent precession of the nuclear fluid spins wherein all radio frequency pulses have carrier frequencies corresponding to the Larmor frequencies of a preselected species of nuclear spins in the fluid molecules. In addition, magnetic field gradients are applied to encode the displacement of fluid molecules during a well-defined time interval $\Delta$. The velocity distribution spectrum, showing the fraction of spins moving at a certain flow velocity, can be obtained from the measured distribution of displacements during the time interval $\Delta$. The fluid transport properties can then be determined from the velocity spectra.

In a preferred embodiment the transport property is the effective porosity of a porous material and is determined by integrating certain portions of the flow velocity distribution spectrum to obtain the fraction of moving and stationary spins and taking the ratio of these quantities.

In another preferred embodiment the transport property is the tortuosity of the flow paths in the porous material determined by the further steps of first measuring the flow velocity distribution along the direction of bulk flow by applying the velocity encoding gradients in the direction of the applied pressure gradient and then in a second experiment by measuring the flow velocity distribution by applying the velocity encoding gradients in a direction perpendicular to the pressure gradient; calculating the velocity distribution spectra for the two experiments and calculating the dispersion of velocities from the velocity spectra; and taking the ratio of the velocity dispersions calculated for the two experiments or comparing the velocity spectra for the two experiments to obtain a measure of the tortuosity.

In another preferred embodiment the transport property is the tortuosity of the flow paths in the porous material determined by the further steps of acquiring velocity spectra for the component of velocity, $v_\perp$, perpendicular to the applied pressure gradient; and by repeating the measurement of the velocity spectra for the component of velocity, $v_\perp$, perpendicular to the applied pressure gradient for at least one more value of the applied pressure gradient; and quantifying the width of the velocity spectrum and using the rate at which the velocity spectrum broadens as a function of flow rate as a measure of the tortuosity.

DESCRIPTION OF THE PREFERRED EMBODIMENT

Figure 1A:
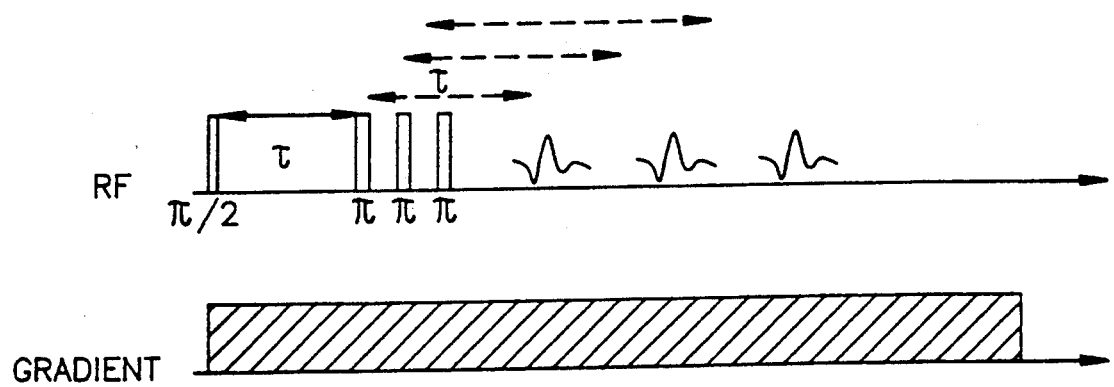
FIG. 1 (a) shows a simple version of a flow encoding spin-echo NMR pulse sequence with constant gradient. The phase evolution is measured by increasing the spin-echo time as indicated in the figure. (b) shows a version with constant spin-echo time, where the magnitude of the magnetic field gradient is incremented between successive spin-echo experiments. (c) shows a version with gradient pulses whose amplitudes are incremented to record the phase evolution for moving spins.

In NMR position and motion are encoded with magnetic field gradients. These gradients refer to the component of the gradient fields along the direction of the applied static magnetic field. The latter is by convention chosen as the z-direction. For the gradients one can therefore write:

$$G_z = \hat{z}\frac{\partial H_z}{\partial z}, G_x = \hat{x}\frac{\partial H_z}{\partial x}$$

and for the y-component, $$G_y = \hat{y}\frac{\partial H_z}{\partial y}.$$

These gradients can be switched on and off in the course of an experiment or can be constant in time. The gradient sign or the polarity of the gradient can be positive or negative and the polarity can change in the course of the experiment. We refer to the time history of the gradient(s) as the gradient waveform and describe it as a function of time with the notation $G_{x,y,z}(t)$.

For a spin moving in a linear magnetic field gradient $G_x$ the phase of the spin is given by:

$$\phi = \gamma \int_0^{t'} x(t)G_x(t)dt \quad (2)$$

x(t) is the time dependent position of the spin. For the most general kind of motion x(t) can be expanded into a Taylor series where the coefficients correspond to the velocity, acceleration etc.:

$$x(t) = x_o + vt + \frac{at^2}{2} + \ldots,$$

where $v$ is the x component of the linear velocity and $a$ is the x component of the linear acceleration and $x_o$ is the starting position. For the phase of the transverse magnetization of the spin this results in:

$$\phi = \gamma x_o \int_0^{t'} G_x(t)dt + \gamma v_x \int_0^{t'} tG_x(t)dt + \quad (3)$$

$$\gamma \frac{a_x}{2} \int_0^{t'} t^2 G_x(t)dt + \ldots$$

The n'th moment of the gradient is defined as:

$$g_n = \int_0^{t'} t^n G(t)dt \quad (4)$$

The phase of the transverse magnetization can then be expressed in terms of moments of the gradient waveform. These gradient waveform moments encode velocity, acceleration and higher derivatives of x(t) as discussed by Nalcioglu and Cho[O. Nalcioglu and Z. H. Cho, *IEEE Transactions in Medical Imaging*, MI-6, 356 (1987)]

For a stationary spin one can image the distribution of spins with a gradient waveform whose zero'th moment is finite. In principle the velocity could be selectively encoded by choosing a gradient waveform for which the first moment of the gradient waveform is finite while all other moments of the gradient waveform are zero. The spatial distribution of velocities can be encoded by choosing gradient waveforms so that both the zeroeth moment of one gradient waveform and the first moment of a second gradient waveform are finite. We define the velocity flow image as the data collected with the combined use of a velocity encoding waveform and a spatial encoding gradient waveform. It is possible to extend these techniques in order to acquire multidimensional data sets where the three spatial dimensions as well as the three components of the velocity are encoded. In practice velocity imaging can be carried out without the nulling of gradient waveform moments higher than the first moment if the experiment is carried out under steady state flow conditions so that the effects of acceleration are negligible.

The gradient waveform $\vec{G}(t)$ can in general be comprised of time independent gradients for which the gradient is constant during the course of the experiment or switched gradients. The application of rf $\pi$ pulses and the polarity of a gradient are both important in calculating the moments of the gradient waveform. A convenient method of accounting for the phase-encoding due to the gradient or the rf pulse is to introduce the effective gradient $G_{eff}(t)$. In the absence of rf $\pi$ pulses $G_{eff}(t) = G(t)$. Each rf $\pi$ pulse inverts the phase of the transverse magnetization. One can account for this in the integral expression for the phase in equation 2 by inverting the sign of the gradient after the application of each $\pi$ pulse. As an example we consider the case of FIG. 1 where a constant gradient is applied. The phase of the transverse magnetization at time $t = 2\tau$ for a stationary spin at position $x_o$ is given by:

$$\phi(2\tau) = \gamma \int_0^{2\tau} x_o G(t) dt = \tag{5}$$

$$\gamma x_o \left[ \int_0^\tau (-G) dt + \int_\tau^{2\tau} (+G) dt \right] = 0$$

This example demonstrates that the application of the $\pi$ pulse reverses the effective polarity of the gradient and despite the fact that a constant gradient is being applied the zeroth moment of the effective gradient in this case is zero. This suggests that the effect of a $\pi$ pulse can also be mimicked by a gradient waveform with two lobes of opposite polarity. This generates what is known as a gradient echo which is equivalent to a spin echo formed with an rf $\pi$ pulse only in the absence of both motion and background gradients. The phase of a spin moving at constant velocity $v_x$ in the x-direction is at time $t = 2\tau$:

$$\phi(2\tau) = \gamma \int_0^{2\tau} v_x t G_x(t) dt = \tag{6}$$

$$\gamma \left[ \int_0^\tau v_x G_x t dt + \int_\tau^{2\tau} v_x t (-G_x) dt \right] = -2\tau^2 G_x v_x$$

For fluids in heterogeneous porous media one generally observes a spin echo signal instead of directly looking at the free-induction signal. The internal background gradients from magnetic susceptibility differences between the fluid and grain material result in a rapid dephasing (i.e. decay) of the free induction signal. For spin-echo signals the effects of constant background gradients are compensated for stationary spins. Therefore echo-signals can be observed on much longer time scales than the free induction decay. The other advantage of spin-echoes is that they allow the experimenter to recall the NMR signal after manipulating the transverse magnetization with gradient pulses to encode position, velocity, acceleration etc.

FIG. 1 shows a simple experimental scheme for encoding of velocity. In this case the gradient is constant and the velocity can be encoded by measuring the echo signal for a set of $\tau$ values. For the purpose of processing the data one would like to have a set of data where the first moment of the gradient waveform has been incrementented with equal steps. For a spin with constant velocity the phase to the first moment of the gradient waveform at the echo-time $2\tau$ is:

$$\phi(2\tau) = \gamma \vec{v_o} \int_0^{2\tau} \vec{G}(t) t \, dt \tag{7}$$

It is convenient to define a vector $\vec{q}(t)$:

$$\vec{q}(t) = \gamma \int_0^t \vec{G}(t') t' \, dt' \tag{8}$$

In an analogous fashion the zero'th moment of the gradient waveform is defined by a vector $\vec{k}(t)$:

$$\vec{k}(t) = \gamma \int_0^t \vec{G}(t') dt' \tag{9}$$

These wave vectors provide a uniform formalism to represent the NMR signal [see P. T. Callaghan, *Principles of Nuclear Magnetic Resonance Microscopy*, Oxford University Press, 1991]. For a distribution of stationary spins described by a density $\rho(\vec{x})$ the total signal $S(\vec{k})$ can be written as:

$$S(\vec{k}) = \int_{\vec{r}} \rho(\vec{r}) \exp[i2\pi \vec{k} \cdot \vec{r}] d^3\vec{r} \tag{10}$$

$$\rho(\vec{r}) = \int_{\vec{k}} S(\vec{k}) \exp[-i2\pi \vec{k} \cdot \vec{r}] d^3\vec{k} \tag{11}$$

These integral relations establish $S(\vec{k})$ and $\rho(\vec{r})$ as Fourier conjugate variables. In an analogous manner one can define a velocity distribution $P(v)$ for an ensemble of spins and establish a conjugate Fourier pair relation between q and $v$ space:

$$S(\vec{q}) = \int_{\vec{r}} P(\vec{v}) \exp[i2\pi \vec{q} \cdot \vec{v}] d^3\vec{r} \tag{12}$$

$$P(\vec{v}) = \int_{\vec{q}} S(\vec{q}) \exp[-i2\pi \vec{q} \cdot \vec{v}] d^3\vec{q} \tag{13}$$

Figure 1B:
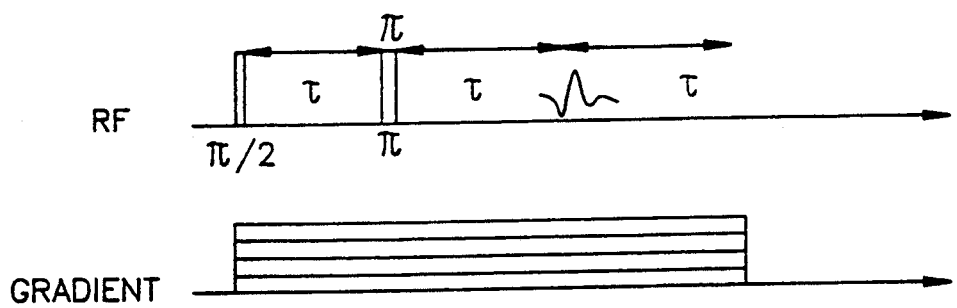
Figure 1C:
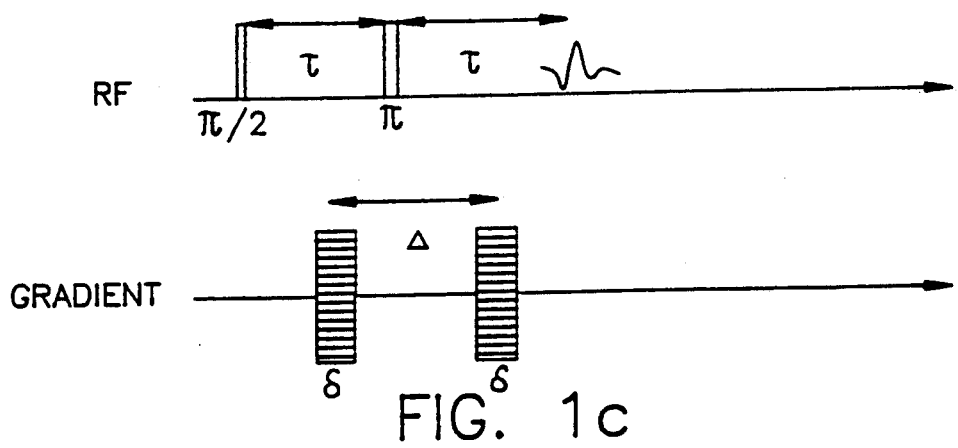

To apply the Fourier transform it is desirable to sample data in uniform intervals in $\vec{q}$ space. Otherwise the data must be interpolated to achieve uniform sampling density so that Fourier transform data processing can be applied. The sequence shown in FIG. 1(a) where the spin-echo time is incremented results in a $\tau^2$ dependence of the first moment and therefore in a quadratically spaced sampling in q space for equal increments of $\tau$. Therefore it is preferable to increment the gradient magnitude and keep $\tau$ fixed. This is shown in FIG. 1(b), where the gradient amplitude is incremented in equal values in the steps of the experiment. These increments are represented in 1(b) by the horizontal lines on the gradient waveform. The presence of the gradient causes a spread of the resonance frequencies of the nuclear spins which now depend on the position of the spin: $\omega_g = \gamma \vec{G} \cdot \vec{r}$. The refocusing pulse, which has a finite duration has a well defined bandwidth $\Delta\omega_{rf}$. For quantitative measurements it is necessary that: $\Delta\omega_{rf} >> \omega_g$. This criteria limits the maximum gradient magnitude which can be used in this sequence. When gradient amplitudes beyond this limit are used, bandwidth artifacts are introduced which adversely affect the ability to quantitatively analyze the data. This limitation can be avoided by the use of switched field gradients such as shown in FIG. 1(c).

Figure 2A:
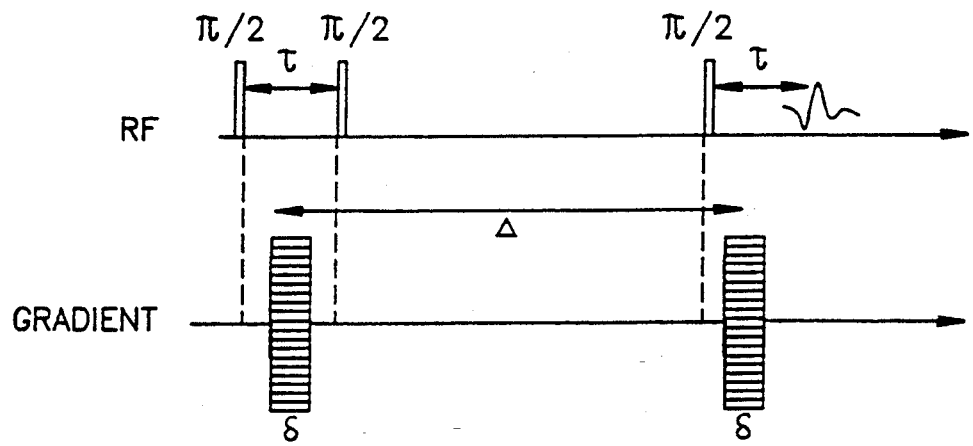
FIGS. 2 (a)-(c) shows three possible stimulated echo pulse sequences to encode flow by the phase encoding method. The stimulated echo is the preferred method over the spin-echo methods shown in FIG. 1 to encode slow flow. FIGS. (b) and (c) are variations of (a) which include $\pi$ pulses and reversal of the gradient polarity to reduce the effects of internal magnetic field gradients. Internal magnetic field gradients are often encountered when heterogenous media such as rocks are placed in a magnetic field.
Figure 2B:
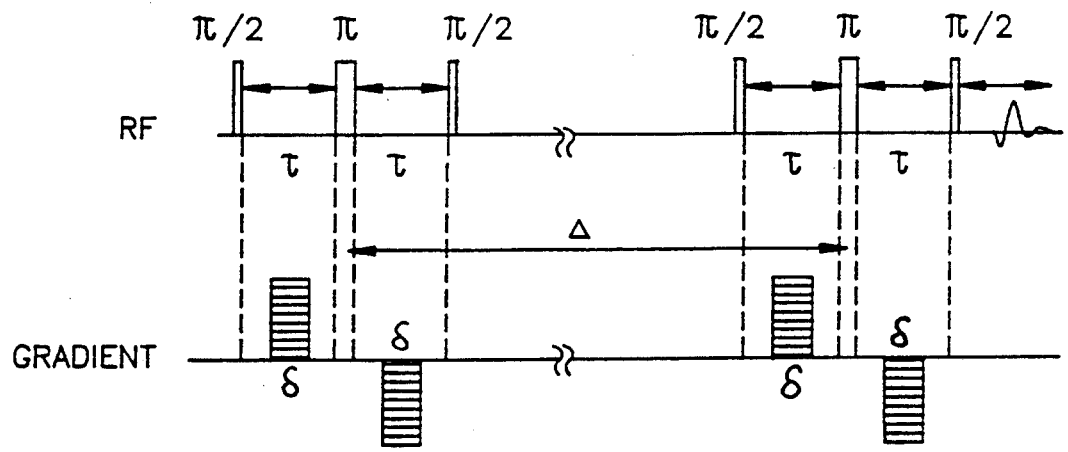
Figure 2C:
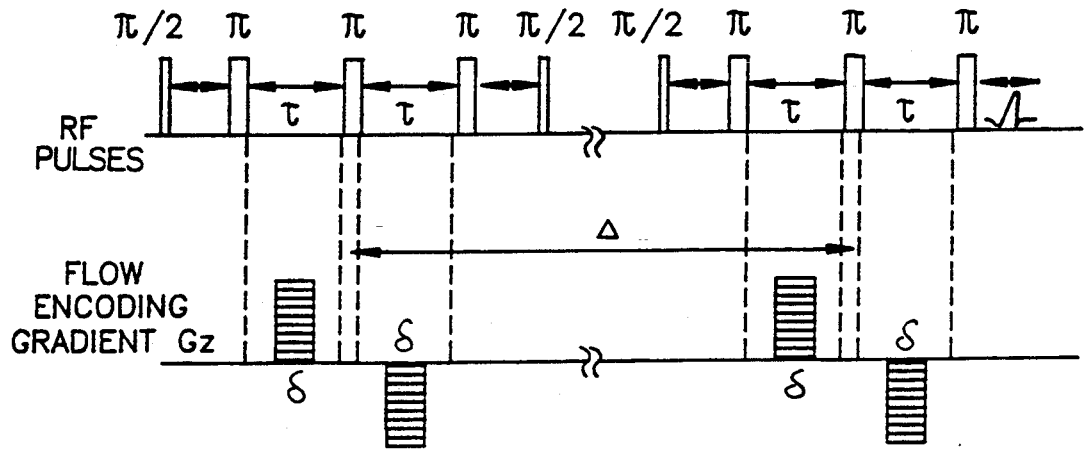
Figure 3A:
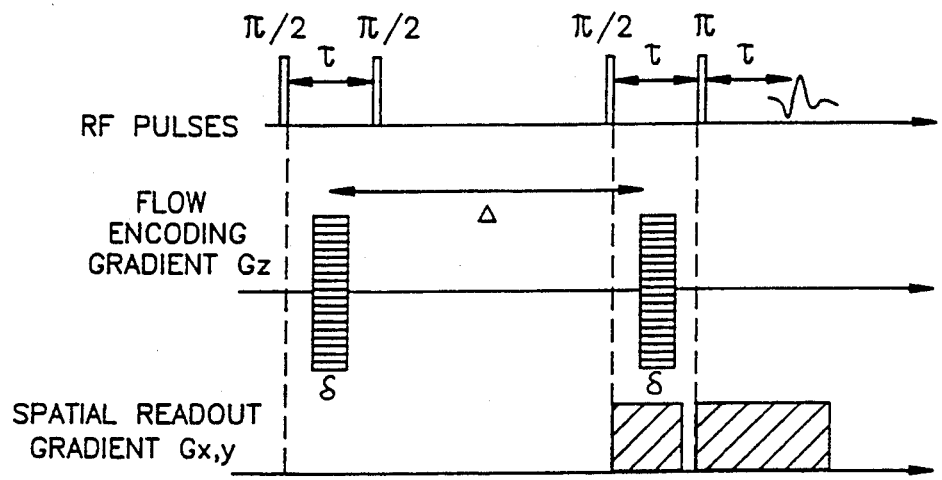
FIGS. 3 (a) and (b) shows pulse sequences analogous to those shown in FIG. 2 (a) and (c) with the addition of magnetic field gradients for the encoding of spatial information.
Figure 3B:
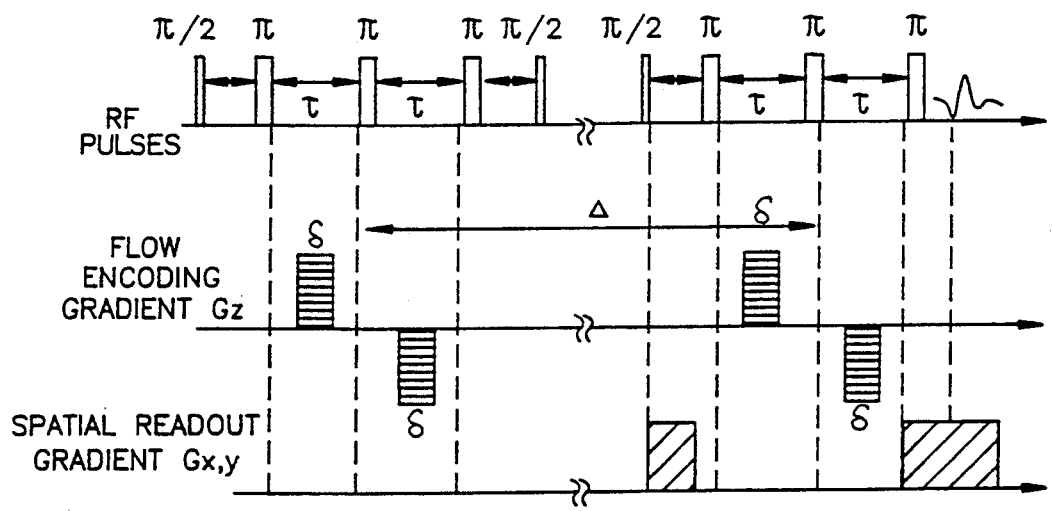

The pulse sequences shown in FIG. 1 are limited by the $T_2$ relaxation time. In most cases the $T_2$ relaxation time is shorter than $T_1$ for fluids in heterogenous media. The encoding of slow flow requires longer evolution times for phase accumulation. It is therefore preferable to use a sequence where $T_1$ rather than $T_2$ is the limiting decay time for the NMR signal. This is possible by using a stimulated echo sequence as shown in FIG. 2. In these pulse sequences the magnetization is stored as longitudinal magnetization during the diffusion time $\Delta$. The magnetization decays exponentially with a rate $1/T_1 < 1/T_2$ during the velocity encoding period.

The susceptibility difference between the fluid flowing in the pore space and the grain material gives rise to magnetic field gradients. As these internal magnetic field gradients are random, often non-linear and not under experimental control it is desireable to cancel the effect of these background gradients. The pulse sequences in FIG. 2(b) and (c) are examples of pulse sequences which cancel the effects of background gradients [R. M. Cotts, M. J. R. Hoch, T. Sun and J. T. Market, *Pulsed field gradient stimulated echo methods for improved NMR diffusion measurements in heterogeneous systems*, Journal of Magnetic Resonance, 83, 252–266 (1989)]. The effect of the background gradients can be cancelled by applying an rf $\pi$ pulse, splitting the gradient pulse into two lobes, and inverting the polarity of the second lobe of the gradient pulse after the $\pi$ pulse. The effective gradient pulse is comprised of two gradient lobes of equal polarity. For the background gradients the $\pi$ pulses cancel their dephasing effect for stationary spins and for moving spins the effect of the background gradients is attenuated. This cancellation or attenuation of the effects of background gradients can be made more effective by increasing the number of $\pi$ pulses inserted during periods of transverse magnetization evolution such as between the first two $\pi/2$ pulses and after the third $\pi/2$ pulse in the stimulated echo sequence.

The basic pulse sequences used to encode motion can be expanded to allow the simultaneous spatial encoding of the signal. This means that instead of obtaining velocity spectra which are characteristic of the whole sample, one now obtains a spectra or velocity information for planes perpendicular to the direction of the spatial encoding gradient. Spatial encoding is achieved with a gradient waveform with non-vanishing zero'th moment. One can either apply a spatial encoding gradient during acquisition of the NMR echo signal or apply a phase-encoding gradient before signal read-out. For the first case with a constant readout gradient $G_x$ the signal being acquired can be written as $$S(t) = \int_{\vec{r}} \rho_\perp(x) \exp[i 2\pi \gamma G_x t x] dx \quad (14)$$

If the echo signal is sampled at a uniform rate one can obtain the density distribution of spins in planes perpendicular to $G_x$ directly from the Fourier transform of $S(t)$. Methods using a read-out gradient are generally faster and therefore preferred over methods using phase encoding gradients. FIG. 2 illustrate the combination of the velocity encoding gradients with the readout-out gradients for spatial encoding. For the phase encoding method the signal being acquired can be represented as shown in equation 10 and the amplitude of the phase encoding gradients is incremented in equal steps. For m phase-encoding steps the excitation and acquisition have to be repeated m times which means that the spatial encoding takes m times as long with the phase encoding method compared with the use of a read-out gradient.

Figure 6:
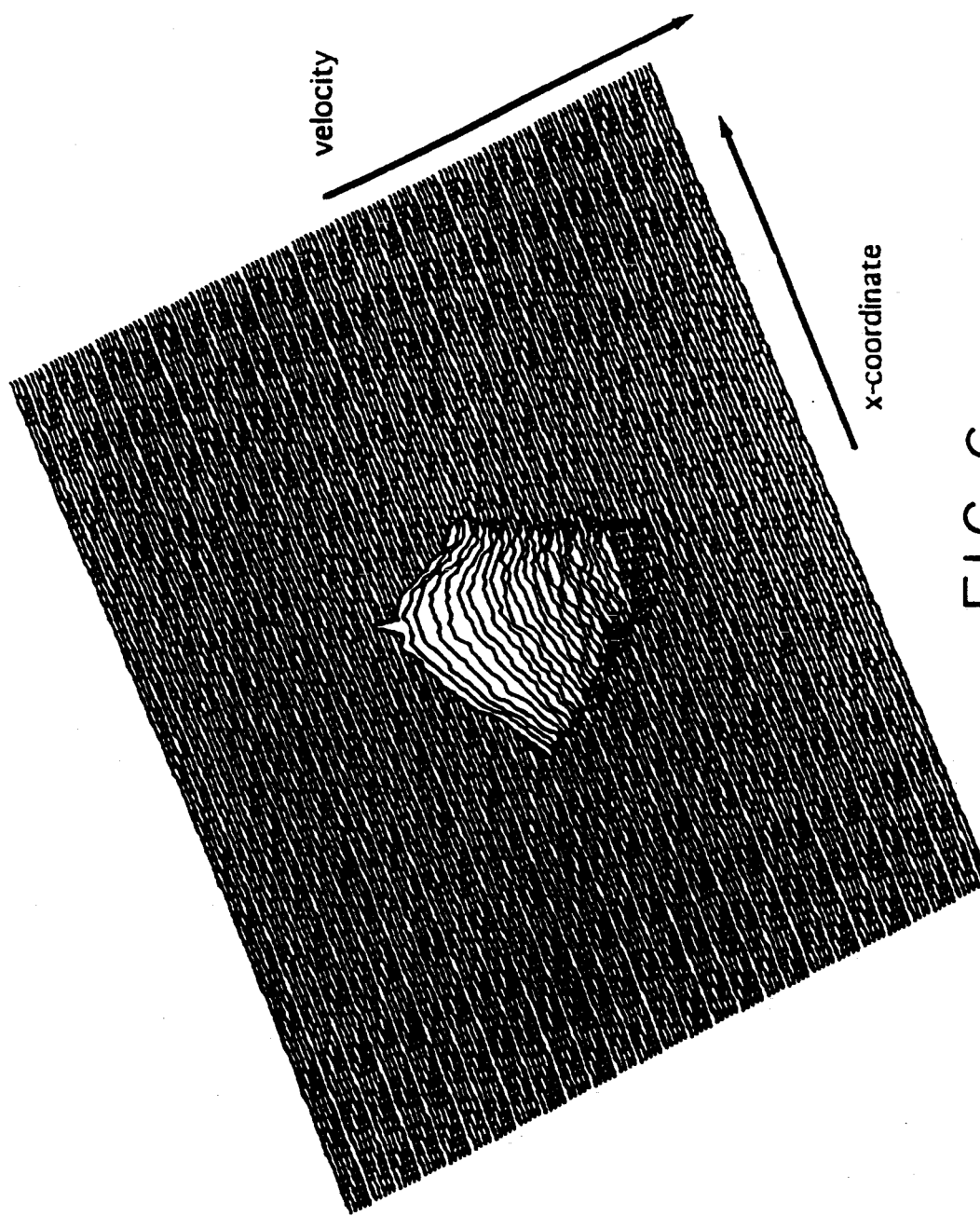
FIG. 6 shows a two dimensional (2-D) spectrum showing spatially resolved velocity spectra for a sandstone rock acquired with the pulse sequence of FIG. 3b.

The combination of recording the NMR signal using both velocity encoding gradients and gradients to encode spatial position results in a multi-dimensional data set. A two-dimensional (2D) data set is obtained if only one spatial dimension is encoded along with the velocity encoding. The 2D data set shown in FIG. 6 is a 2D Fourier transform where one Fourier transform is with respect to the velocity encoding gradient and the second Fourier transform is with respect to the spatial encoding gradient. For the spatially resolved velocity spectrum shown in FIG. 6 flow in the z direction was encoded with the gradient $G_z$ while the spatial information was encoded with a readout gradient $G_x$. The third dimension in FIG. 6 represents the relative number of spins at position x with velocity $v_z$. The sample was a cylindrical core plug of sandstone rock which had been sealed on the sides and connected to in-flow and out-flow tubes at both ends. The spatially resolved velocity image shows that the velocity is largest at the center of the sample and falls off to zero at the edges. The image shows that the flow profile characteristic for laminar flow in a tube is still recognizable when the fluid moves through the sandstone plug. This is consistent with the very high permeability and large pore connectivity of this rock sample. Velocity spectra for a certain position x can be obtained from this spatially resolved velocity image data set by taking a slice along the velocity axis.

Methods for improved control of the region of the sample which is selectively excited by rf pulses have been developed. These techniques include slice selection obtained by combined use of shaped rf and gradient pulses. Such methods are also applicable to the techniques described in this invention and can be used to measure spatially localized fluid flow transport properties described in this invention.

When only velocity encoding is used, the distribution of velocities for a fluid pressure drop across the sample can be measured. When no spatial encoding is used, the velocity spectrum measured arises from the region of the sample within the sensitive volume of the rf coil volume. The pressure drop across the sample establishes a specific fluid flow rate. Several velocity spectra recorded for a number of fluid flow rates for the same sandstone core plug are shown in FIG. 4.

Figure 4:
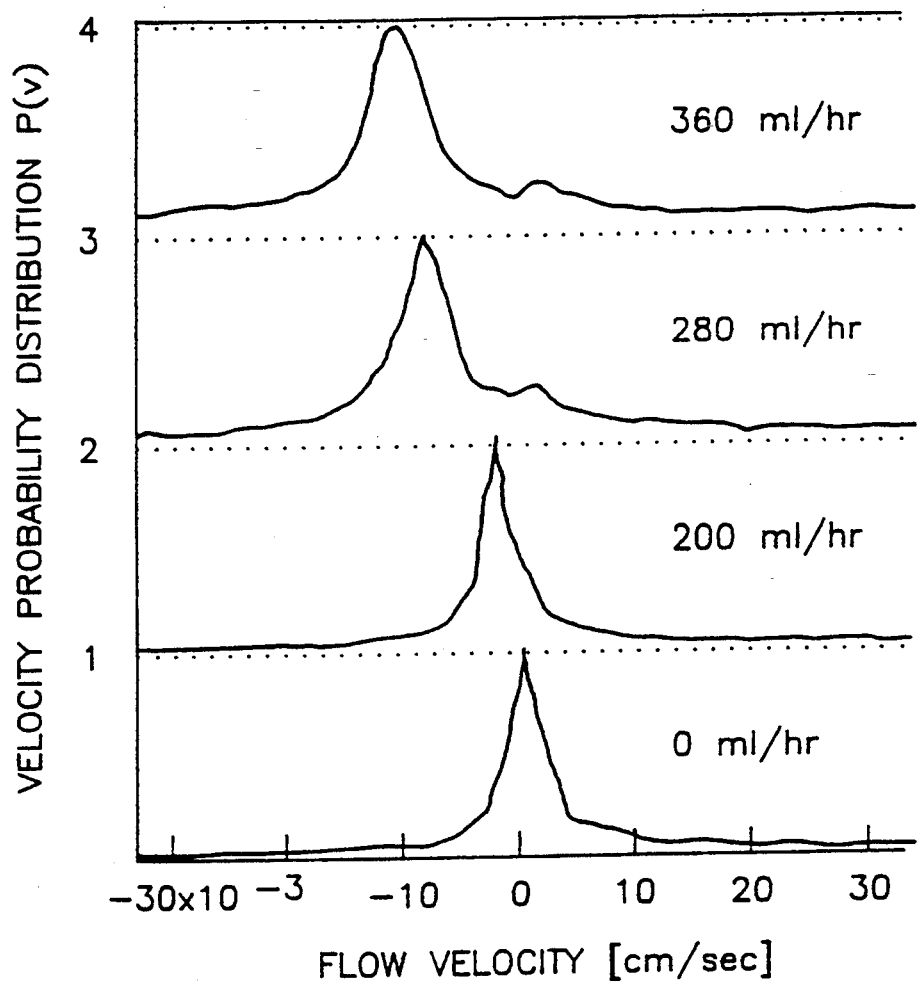
FIG. 4 shows velocity spectra acquired at different fluid flow rates for a sandstone sample. The velocity peak at zero velocity observed for flow rates of 280 ml/hr and 360 ml/hr originates from fluid which does not contribute to bulk flow.

The velocity spectrum recorded under conditions of no fluid flow, shown in FIG. 4 arises from the fluid self diffusion [see J. Kaerger, H. Pfeiffer and W. Heink, "Principles and Application of Self-Diffusion Measurements by Nuclear Magnetic Resonance", *Advances in Magnetic Resonance*, 12, 1–89 (1988)]. The velocity peak is centered at zero velocity consistent with the fact that there is no net fluid flow. The width of the peak is determined by the random motion of the fluid. The scaling of the velocity axis can be calculated from a calibration experiment where water is flowing through a tube of known dimensions at a controlled flow rate. Alternatively, the scaling of the axis can be calculated from the first moment of the gradient pulses which have a known duration and strength. In this case, the magnetic field gradient strength must be determined experimentally such as from NMR imaging an object with known dimensions or from pulsed field gradient NMR measurements of fluid diffusion for a fluid with a known diffusion constant.

In velocity spectra recorded under conditions of fluid flow, the velocity probability distribution displays directly the fraction of spins flowing at a given velocity. In the velocity spectra for the sanstone core plug recorded at higher flow rates shown in FIG. 4, most proton spins (on the water molecule) are seen to have a well defined average velocity. This average velocity is given by the position of the maximum of the peak in each velocity spectrum. At higher flow rates, the peak shifts to positions along the velocity axis corresponding to higher velocities.

In the spectra of FIG. 4, it is apparent that a velocity peak is observed at zero velocity even at the highest flow rates. The peak at zero velocity arises from fluid which is not contributing to bulk flow. A likely source of this none flowing fluid is the fluid in pores which are not well connected to the flow path in the porous medium. An example of poorly connected pores are "dead end" pores. The peaks in the velocity spectrum corresponding to the fractions of the non-flowing and flowing fluid may be well resolved or may overlap depending on the fluid flow rate determined by the pressure drop along the direction of flow. One methods for quantifying the fraction of fluid contributing to bulk flow and none flowing fluid is to choose the minimum between the two velocity peaks as the boundary for the limit of integration for the respective areas under the peaks. The effective porosity can be calculated from the ratio of the areas determined from these two integrals. The effective porosity is that fraction of the total porosity which contains fluid that contributes to bulk fluid flow. The total porosity is the volume fraction of the porous material that contains fluid when the porous material is saturated with fluid. The effective porosity is an important parameter for estimating the fraction of fluid which can be recovered from fluids in a porous material such as a reservoir rock containing petroleum.

Figure 5:
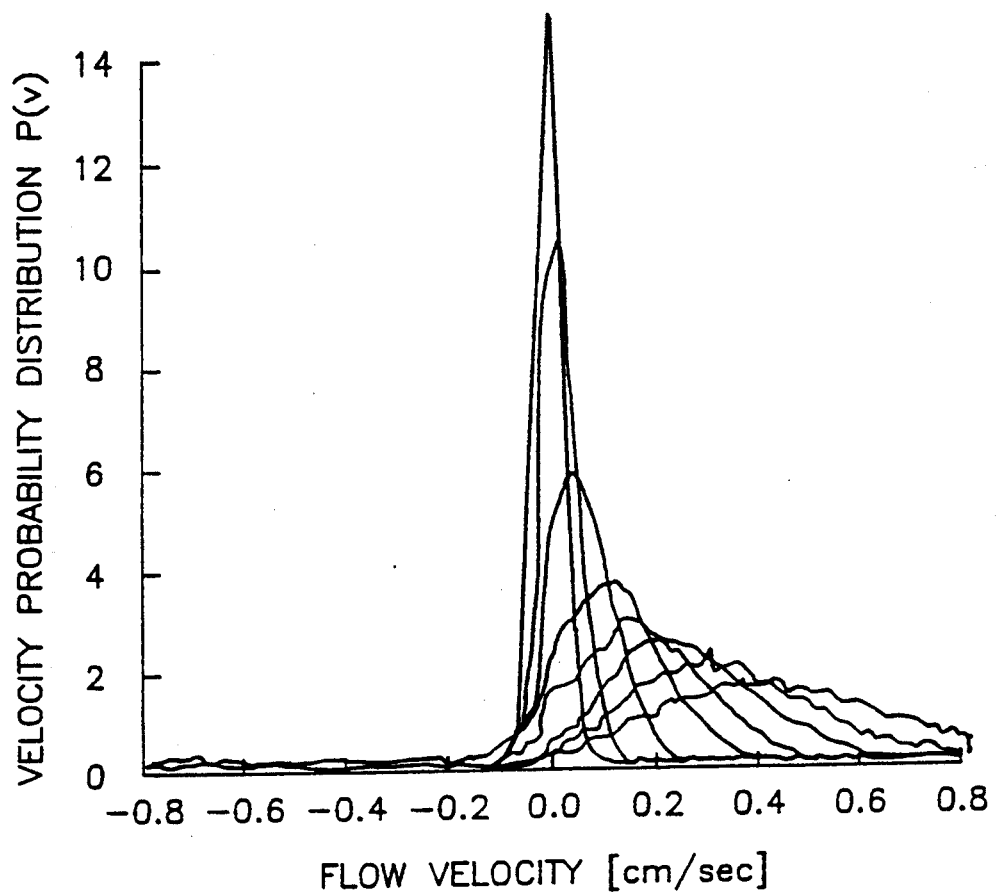
FIG. 5 shows velocity spectra acquired at different fluid flow rates for a sample of sintered glass beads where the effective and total porosity are about the same due to the absence of dead-ended pores.

As a comparison to the spectra in FIG. 4, FIG. 5 shows the velocity spectra for a sintered glass bead pack where the fraction of dead-ended pores is negligible. Accordingly no peak at zero velocity is observed at flow velocities which are high enough so that the peak at finite velocity no longer overlaps with any spectral features at zero velocity.

Figure 7:
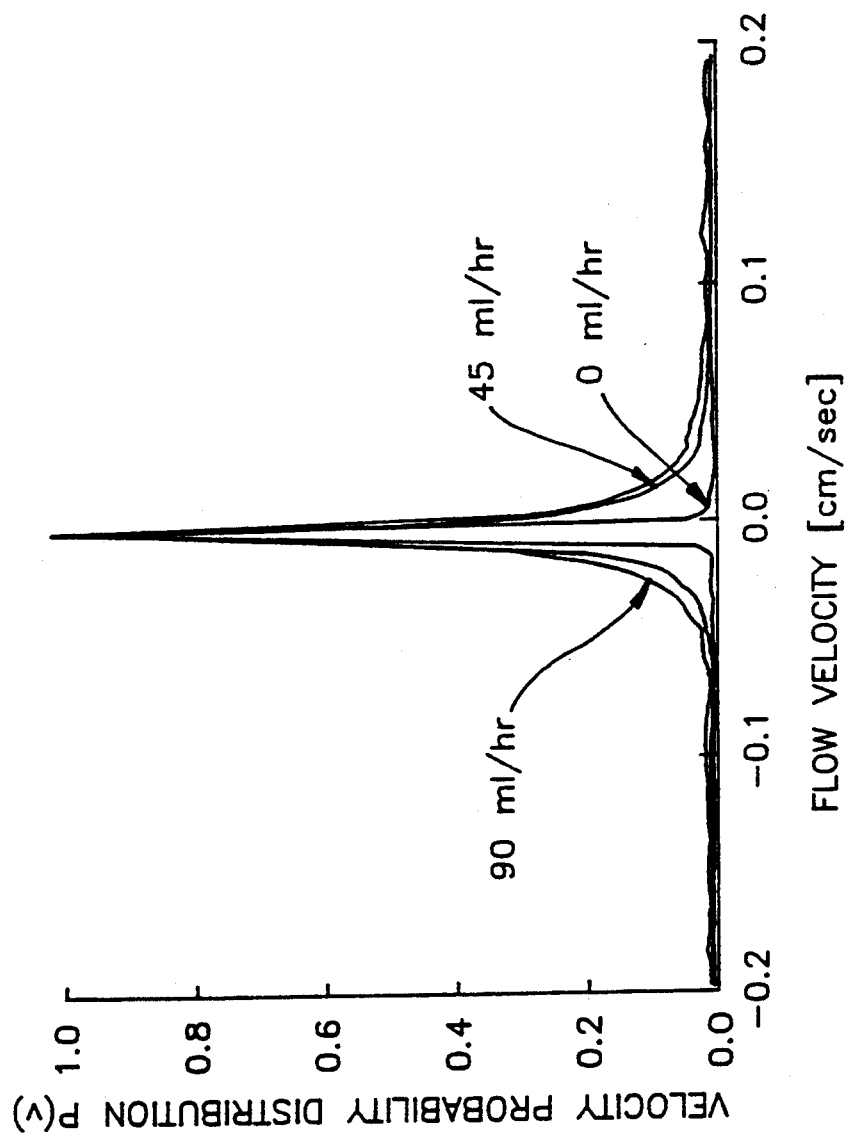
FIG. 7 shows velocity spectra acquired at several flow rates for a component of the velocity perpendicular to the applied pressure gradient.

The spectra of FIG. 7 show velocity spectra where the velocity encoding is along a direction perpendicular to the direction of the applied pressure gradient. As bulk motion of fluid spins takes place only in the direction of the applied pressure gradient the velocity spectra for a direction perpendicular to the applied pressure gradient should be centered at zero velocity. The spectra will also be symmetric about $v_\perp = 0$, where $v_\perp = 0$ is the component of fluid flow velocity along a direction perpendicular to the direction of the applied pressure gradient, if the angular distribution of flow paths is isotropic. The acquisition of the velocity spectra for velocity components $v_\perp$ can therefore provide an indication of anisotropies and heterogeneities in the spatial distribution of flow paths, even in the absence of spatial encoding.

A comparison of the velocity spectra for the fluid flow velocity, $v_\|$, parallel to the direction of the applied pressure gradient to the fluid flow velocity, $v_\perp$, perpendicular to the applied pressure gradient can also provide a measure of the tortuosity. The measurement of tortuosity is useful for pore network modeling, for fundamental predictions of the components of permeability and for reservoir simulation. The tortuosity, T, is the ratio of the average effective length $L_e$ of a flow path and the net displacement L in the direction of the applied pressure gradient [F. A. L. Dullien, *Porous Media: Fluid Transport and Pore Structure*, Academic Press, New York (1979)] The latter is the length of the shortest path connecting the beginning and end points of the effective flow path:

$$T = L_e/L \tag{15}$$

In these velocity flow experiments the tortuosity is defined for paths corresponding to a net displacement in the direction of the applied pressure gradient. The flow path can be thought of as consisting of infinitesimally small segments (dl) which can be written in terms of components parallel and perpendicular to the direction of the applied pressure gradient ($dl = \sqrt{dl_\|^2 + dl_\perp^2}$). In terms of these infinetesimal fluid displacements, the tortuosity can then be defined as:

$$T = \frac{\sum_i \sqrt{dl_{\|,i}^2 + dl_{\perp,i}^2}}{\sum_i dl_{\|,i}} \tag{16}$$

where the index i numbers the subsequent displacements along the flow path and the numerator is the total displacement while the demoninator is the displacement along the direction of the applied pressure gradient. In the actual experiment we measure the probability distribution for displacements parallel and perpendicular to the applied pressure gradients of all the fluid spins moving in the pore space. An operational formula to calculate the tortuosity from these probability distributions for parallel and perpendicular displacement $P_\|(l)$ and $P_\perp(k)$ is:

$$T = \frac{\int_{-\infty}^{\infty} \int_{-\infty}^{\infty} P_\|(l) P_\perp(k) \sqrt{l^2 + k^2}\, dl\, dk}{\int_{-\infty}^{\infty} P_\|(l) dl \int_{-\infty}^{\infty} P_\perp(k) dk} \tag{17}$$

where the numerator is the average total displacement and the demoninator is the average displacement along the direction of the applied pressure gradient. For straight flow lines in the direction of the applied pressure gradient and the case where the flow is fast enough that diffusion can be neglected: $P_\perp(k) = \delta(k)$. Inserting this into the above equation yields the result $T = 1$ as expected for this limiting case. These probability distributions $P_{\parallel}(l)$ and $P_{\perp}(k)$ only require measurement at one flow rate and should in fact be measured at the same flow rate.

The displacement is measured using a bipolar magnetic field gradient where the lobes of the gradient have a width $\delta$ and the time which separates the two lobes of the gradient is denoted by $\Delta$. The range of values for these parameters is from 200 to 1,000 microseconds for $\delta$ and 50 to 800 milliseconds for $\Delta$. The sensitivity to the displacement is determined by the first moment of these bipolar gradients and the first moment is a linear function of the amplitude of the gradient lobes. Typical values for the amplitude of the gradient are 1 to 20 Gauss/cm.

The measurement of $P_{\perp}(l)$ for several fluid flow rates provides an alternative method for measuring the tortuosity of a porous material. A measure of the mean square displacement perpendicular to the direction of the applied pressure gradient can be obtained from the measured $P_{\perp}(l)$ by integration:

$$<l_{\perp}^2> = \frac{\int_{-\infty}^{\infty} P_{\perp}(l)(l - <l_{\perp}>)^2 dl}{\int_{-\infty}^{\infty} P_{\perp}(l) dl} \quad (18)$$

where $[l_{\perp}]$ is the average perpendicular displacement. The quantity $[l_{\perp}^2]$ is also equivalent to the second moment of the displacement probability distribution. The second moment is also a measure of the dispersion of the fluid flow. In an isotropic porous material, fluid displacements in any direction perpendicular to the direction of the applied pressure gradient are all equally probable. The average displacement, $[l_{\perp}]$ will therefore be zero for most random porous media since a displacement of $-l_{\perp}$ is equally probable to a displacement of $+l_{\perp}$. Exceptions can occur for stratified media where the permeability is not a scalar but is instead described by a tensor. For flow through a straight capillary and in the limit of low Reynolds numbers where no turbulence occurs, the second moment of the displacement probability distribution ($[l_{\perp}^2]$) is not expected to change with a change in flow rate. In this case the tortuosity is equal to 1 since the fluid molecules (which carry the spins) flow along the shortest path between two points on a line parallel to the direction of flow. For a porous medium where the tortuosity number is larger than one, the second moment of the displacement probability distribution ($[l_{\perp}^2]$) will increase with increasing flow rate. The rate of change of the second moment (i.e., the dispersion) of the displacement probability distribution ($[l_{\perp}^2]$) can be used as an alternative measure of the tortuosity. Explicit relations of the longitudinal and transverse dispersion as a function of average flow velocity for fluid flow through porous media are known in the literature [see J. Bear, *Dynamics of Fluids in Porous Media*, Elsevier, New York, 1972; and also M. Sahimi, B. D. Hughes, L. E. Scriven, and H. T. Davis, *Dispersion in Flow Through Porous Media—Part I: One Phase Flow*, Chemical Engineering Science, vol. 41, 2103-2122 (1986)].

Further spatial localization of the signal can be achieved by using slice selective rf pulses. The pulses are generally applied at the Larmor frequency of the selected nucleus and by applying the pulses in the presence of a linear gradient which makes the precession frequency depend on the linear coordinate in the direction of the gradient one can excite only the spins in a slice. The thickness of the slice is defined by the bandwidth of the rf pulse and the strength of the linear magnetic field gradient. To excite spins in a slice of thickness $\Delta \vec{r}$ one has to use an rf pulse with a bandwidth $\Delta \omega_{rf}$ such that:

$$\Delta \omega_{rf} = \gamma \vec{G} \cdot \Delta \vec{r} \quad (19)$$

A different method of measuring the movement of fluid or the distribution of flow velocities is provided by the time-of-flight method. In this method one prepares spins in a well defined region with a sequence of rf pulses. One could for example saturate all spins in a slice of well defined thickness and then image the distribution of unsaturated spins which have been moved by the flow into that same slice. This method therefore does not use flow encoding gradients and because of this the calculation of velocity spectra is less straight forward. A detailed discussion can be found in several review papers on medical angiography where the time-of-flight method has proven to be very useful.

For the all flow encoding experiments in the laboratory, it is useful to cut out a cylindrical plug of the porous material to be investigated and seal all surfaces except the end caps of the cylinder. Tubing is connected to the plug at both ends and the pump which controls the flow rate of fluid is connected. The plug with the attached tubes is placed in the NMR magnet.

The methods described in this invention can also be used in the investigation of earth formations using NMR logging tools. NMR logging tools can produce the rf pulse sequencing and magnetic field gradients required for the fluid flow transport properties measurements described in this invention. Fluid flow in the earth formation can be induced by applying pressure pulses in the earth formation which are synchronized with the rf pulses in the presence of constant magnetic field gradients or synchronized with pulsed magnetic field gradients.

What is claimed is:

1. A method for obtaining at least one fluid transport property of a porous material under steady flow conditions comprising:
   (a) saturating the porous material with a fluid and imposing a pressure gradient such that fluid flows through the porous medium;
   (b) applying NMR radio frequency pulses leading to a coherent precession of the nuclear fluid spins wherein all radio frequency pulses have carrier frequencies corresponding to the Larmor frequencies of a preselected species of nuclear spins in the fluid molecules;
   (c) applying magnetic field gradients to encode the displacement of fluid molecules during a well-defined time interval $\Delta$;
   (d) measuring the distribution of fluid displacements during said time interval $\Delta$;
   (e) determining said fluid transport property from said distribution of fluid displacements, wherein said transport property is effective porosity and tortuosity.

2. The method of claim 1 wherein said transport property is the effective porosity of a porous material determined by integrating certain portions of said distribution of fluid displacements to determine the fraction of moving and stationary spins and taking the ratio of these quantities to obtain the effective porosity.

3. The method of claim 1 wherein said transport property is the tortuosity of the flow paths in the porous material and wherein the step of applying the fluid displacement encoding gradients of 1(c) are applied in the direction of the applied pressure gradient and then in a direction prependicular to the pressure gradient, and wherein the fluid transport property of 1(e) is the tortuosity obtained by taking the ratio of the average total displacement to the component of the displacement in the direction of the applied pressure gradient.

4. The method of claim 1 wherein said transport property is the tortuosity of the flow paths in the porous material and wherein the step of applying the fluid displacement encoding gradients of 1(c) are applied in a direction perpendicular to the applied pressure gradient and wherein step 1(c) is repeated for at least one more value of the applied pressure gradient, and wherein the fluid transport property of 1(e) is the tortuosity obtained by measuring the change of the second moment of the displacement probability distribution.

5. The method of claim 1 (b) where said NMR radio frequency pulses are a stimulated echo sequence.

6. The method of claim 1 wherein said NMR radio frequency pulses in step (b) uses $\tau$ rf pulses and reversal of the gradient polarity to reduce the effects of background gradients present when porous materials are placed in a magnetic field.

7. The method of claim 1 wherein the fluid spin displacements are phase-encoded with switched magnetic field gradients such that the integral over the effective gradient waveform is nulled to encode only relative displacements and not the positions of fluid molecules during a well-defined time interval.

8. The method of claim 1 wherein the said gradients are constant during the course of the experiment and the motion is quantified by measuring the spin echo as a function of the echo delay time.

9. The method of claim 1 wherein the relative displacement of spins is encoded with a time-of-flight technique wherein a selected population of nuclear spins in a spatially well defined region are prepared by applying one or a plurality of radio frequency pulses and imaging the spatial distribution of said spins after a well-defined time interval.

10. The method of claim 1 wherein the measurements are carried out with additional magnetic field gradients being applied to obtain spatially resolved information about the distribution of fluid molecule displacements.

11. The method of claim 1 wherein the measurement is performed down hole with an NMR logging tool to measure fluid motion in earth formations.

* * * * *